(12) United States Patent
Schmelzeisen-Redeker et al.

(10) Patent No.: US 8,523,894 B2
(45) Date of Patent: Sep. 3, 2013

(54) SYSTEM FOR WITHDRAWING BODY FLUID

(75) Inventors: Guenther Schmelzeisen-Redeker, Lorsch (DE); Thomas Weiss, Mannheim (DE); Frank Deck, Niederkirchen (DE); Klaus Peter Ebert, Frankisch-Crumbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 743 days.

(21) Appl. No.: 11/903,711

(22) Filed: Sep. 24, 2007

(65) Prior Publication Data

US 2008/0021494 A1 Jan. 24, 2008

(51) Int. Cl.
- *A61B 17/14* (2006.01)
- *A61B 17/32* (2006.01)
- *A61B 5/00* (2006.01)
- *B65D 81/00* (2006.01)
- *A61M 5/00* (2006.01)

(52) U.S. Cl.
USPC ........... 606/181; 600/583; 600/587; 604/115; 604/116; 604/117

(58) Field of Classification Search
USPC ............... 600/583, 584; 604/101.05, 103.03, 604/115–117; 606/181
See application file for complete search history.

(56) References Cited

U.S. PATENT DOCUMENTS

| | | | |
|---|---|---|---|
| 2,646,799 A | 2/1951 | Jacoby, Jr. ................ | 128/314 |
| 3,626,929 A | 12/1971 | Sanz et al. ................ | 128/2 R |
| 3,741,197 A | 6/1973 | Sanz et al. | |
| 4,151,832 A * | 5/1979 | Hamer .................... | 600/578 |
| 4,634,427 A * | 1/1987 | Hannula et al. ......... | 604/288.02 |
| 5,014,718 A * | 5/1991 | Mitchen .................. | 600/584 |
| 5,026,388 A | 6/1991 | Ingalz ..................... | 606/182 |
| 5,070,886 A * | 12/1991 | Mitchen et al. ......... | 600/584 |
| 5,201,324 A * | 4/1993 | Swierczek ............... | 600/583 |
| 5,248,304 A * | 9/1993 | Vigdorchik et al. ..... | 604/278 |
| 5,320,607 A * | 6/1994 | Ishibashi ................. | 604/115 |
| 5,324,302 A | 6/1994 | Crouse .................... | 606/181 |
| 5,505,212 A * | 4/1996 | Keljmann et al. ....... | 600/584 |
| 5,582,184 A | 12/1996 | Erickson et al. ........ | 128/763 |
| 5,624,458 A | 4/1997 | Lipscher ................. | 606/181 |
| 5,682,233 A | 10/1997 | Brinda .................... | 356/246 |
| 5,709,699 A * | 1/1998 | Warner ................... | 606/181 |
| 5,746,217 A | 5/1998 | Erickson et al. ........ | 128/760 |
| 5,820,570 A | 10/1998 | Erickson et al. ........ | 600/573 |
| 5,951,493 A * | 9/1999 | Douglas et al. ......... | 600/583 |
| 6,080,116 A | 6/2000 | Erickson et al. ........ | 600/573 |
| 6,152,889 A | 11/2000 | Sopp et al. .............. | 600/578 |
| 6,306,104 B1 | 10/2001 | Cunningham et al. ... | 600/573 |
| 6,589,260 B1 * | 7/2003 | Schmelzeisen-Redeker et al. ................. | 606/181 |
| 7,291,159 B2 * | 11/2007 | Schmelzeisen-Redeker et al. ................. | 606/181 |

FOREIGN PATENT DOCUMENTS

| | | |
|---|---|---|
| EP | 0 575 952 | 12/1993 |
| EP | 0988828 B1 | 7/2008 |
| JP | 10033508 | 2/1998 |
| PL | 165354 | 1/1992 |

(Continued)

*Primary Examiner* — Alireza Nia
(74) *Attorney, Agent, or Firm* — Roche Diagnostics Operations, Inc.

(57) ABSTRACT

The present invention relates to a compression device for stimulating the efflux of a body fluid from a body part. The device has a compression unit with a pressure-application region made of a deformable material, the region being formed to generate a repulsive force between the body part and the compression unit. The repulsive force passes through a force maximum then decreases to serve as an indication that the body part is guided sufficiently firmly and far enough onto the compression unit.

6 Claims, 5 Drawing Sheets

(56) References Cited

FOREIGN PATENT DOCUMENTS

| WO | 95/10977 A1 | 4/1995 |
| WO | 9704707 A1 | 2/1997 |
| WO | WO 97/42886 | 11/1997 |
| WO | WO 97/42888 | 11/1997 |
| WO | WO 97/43962 | 11/1997 |
| WO | 9746157 A1 | 12/1997 |
| WO | 9824366 A3 | 6/1998 |
| WO | WO 99/26539 | 6/1999 |

* cited by examiner

SYSTEM FOR WITHDRAWING BODY FLUID

REFERENCE TO RELATED APPLICATIONS

This application claims priority to U.S. patent application Ser. No. 10/409,827, filed on Apr. 9, 2003, which is a continuation of U.S. Pat. No. 6,589,260 issued Jul. 8, 2003.

TECHNICAL FIELD

The present invention concerns a system for withdrawing body fluid from a part of the body, especially the finger pad.

BACKGROUND OF THE INVENTION

Body fluids are primarily withdrawn for a subsequent analysis in order to diagnose diseases or to monitor the metabolic state of a patient. Such a withdrawal is carried out especially by diabetics in order to determine the blood sugar concentration. The aim of such a blood-sugar check that is usually carried out several times daily is to avoid hypoglycaemic states as well as hyperglycaemic states. In the case of a hypoglycaemia the patient can fall into a coma and even die since the brain is no longer adequately supplied with glucose. In contrast hyperglycaemic states can lead to long-term side-effects such as blindness, gangrenes and such like.

Consequently a frequent monitoring of the blood sugar level is an undisputed necessity. It is therefore obvious that there is an urgent need for sampling systems which are easy to operate by the user and are above all largely free of pain.

Already blood sampling systems have been known for some time in the prior art which allow the patient or hospital staff to carry out a withdrawal in a simple manner. A device suitable for this is for example the commercially available Softclix whose manner of operation is described in U.S. Pat. No. 5,318,584. This device provides an adjustment means for the depth to which a lancet is inserted into the tissue. Hence the patient can select the minimum puncture depth which enables a just sufficient quantity of blood to be obtained for a subsequent analysis and thus keep the incision pain very low. After the patient has produced a skin opening by piercing, he has to massage or press his finger in order to draw sufficient blood from the puncture wound especially with small puncture depths. This operation which is frequently referred to as "milking" by diabetics can hitherto only be avoided when the puncture is very deep and correspondingly unpleasant for the patient and can lead to major scarring on the sensitive finger tips. Devices known in the prior art attempt to stimulate the outflow of blood by applying a vacuum but this has proven to be not efficient.

Devices are also known in the prior art in which a so-called stimulator with a ring depresses the skin surface surrounding an incision site. Such a device for obtaining interstitial liquid is described for example in U.S. Pat. No. 5,582,184. The ring used to depress the skin surface is made of a rigid material. Only small amounts of fluid can be obtained with the device that are not adequate for commercial analytical systems.

Another device is known from U.S. Pat. No. 5,857,983 in which a syringe is inserted into the skin surface and the skin surface surrounding the site of incision is repeatedly depressed using a so-called stimulator in order to press body fluid into the syringe. Like the above-mentioned document a rigid ring is used in this device to depress the skin surface. The amounts of body fluid that can be obtained with this device are small and thus inadequate for conventional analytical systems.

Blood sampling devices are also described in the U.S. Pat. No. 5,951,493 which operate with a stimulator like the above-mentioned US patent. In addition a device is described in FIGS. 15 to 17 in which the area of the device that is used to press against a body surface is provided with levers (104) which laterally press together a part of the body while the device is pressed against the body surface. The devices described in this patent are in particular intended for withdrawing body fluids from other sites than the finger pad. In addition the document shows that the transport of body fluid onto the skin surface is achieved by repeated pressing of the device.

A device is known from the document U.S. Pat. No. 3,626,929 in which a finger is clamped before blood withdrawal between a lever and a finger support. The finger support is moved by a motor in order to result in a massaging proximal to the incision site. For the withdrawal the user's finger is pressed against a flexible cap in which needles and a fluid channel are located. A disadvantage of this device is that the needles for the withdrawal remain in the body and that in this state the finger support is moved. This results in the movement of the needles in the finger which usually leads to considerable pain. In addition it is extremely unlikely that blood will emerge while there is a needle in the finger so that the channel is closed by the needle. A collecting container is shown in FIGS. 11 and 12 which has a flexible pressure-application region. However, due to the shape of the pressure-application region which widens conically towards the finger there is no conversion of a primary pressure-application movement into a lateral movement which squeezes the sampling region together.

SUMMARY OF THE INVENTION

The object of the present invention was to provide a system for withdrawing body fluid which, using small puncture depths, yields an adequate amount of body fluid, in particular blood. An additional object of the invention was to provide a system which can be easily operated and has a simple construction. Simplicity in this sense means in particular that the number of operating steps is as small as possible.

A further object of the invention is in particular to simplify blood withdrawal from the finger pad and in doing so take into account different finger sizes and different puncture sites on the finger tip.

Consequently the present invention concerns a system for withdrawing body fluid from a part of the body in particular a finger pad comprising the following elements: a compression unit against which a body part is pressed in a primary direction and partially converts the applied pressure into a movement in a secondary direction with a component perpendicular to the primary direction such that the internal pressure is increased in a region of said body part, a perforation device, in particular a lancet or needle to produce a body opening in the region of the increased internal pressure, wherein the compression unit has a pressure-application region made of a deformable material.

The invention additionally includes a system for stimulating the outflow of body fluid from a body part, a process for stimulating outflow of body fluid and a process for withdrawing body fluid.

Use of the compression unit according to the invention enables the above-mentioned milking movement to be simulated in a simple and convenient manner for the user in order to squeeze out blood from the incision site. The compression unit not only yields larger quantities of body fluid than is the case with the compression devices of the prior art but the compression and withdrawal process is also considerably more pleasant for the patient. This is due to the fact that the compression unit fits snugly around the body part, in particular a finger. A further contributing factor is that the compression unit enables adequate quantities of body fluid to be obtained even with very small puncture depths.

An additional very important advantage of the present invention is that use of a compression unit with a pressure-application region made of deformable material enables body fluid to be withdrawn with the compression unit from body parts of various shapes in a reliable and pleasant manner. In particular it easily and reliably enables withdrawal from fingers of different sizes. In addition the deformable material compensates for differences in the shape of the pressed body part (finger tip versus side of the finger).

The system according to the invention can be used particularly advantageously to obtain capillary blood from the finger pad. In addition it is also possible to withdraw blood or interstitial fluid from other body parts such as the arm.

An essential element of the system is the compression unit which results in the body part being squeezed together not only in the direction of the primary applied pressure but also results in the applied pressure being at least partially diverted such that a squeezing occurs with components of force transverse to the primary direction of pressure-application. As a result the region of the body part from which the withdrawal is to take place is pressed together laterally. The mode of action of this advantageous compression is elucidated later on the basis of the embodiments. The compression unit produces an increase of the internal pressure in a region of the body part. This region of increased internal pressure is adjacent to the region on which the applied pressure acts, or is surrounded by the region of applied pressure. A perforation device can now be used to perforate the region of increased internal pressure and remove body fluid.

The compression unit comprises a pressure-application region made of deformable material. On the one hand such a material makes the withdrawal process more pleasant for the user and, on the other hand, it also enables an easier adaptation to the various shapes and sizes of the body parts. Deformable plastics such as elastomers, rubbers and such like can for example be used as materials for the pressure-application region. The pressure-application region is preferably ring-shaped. This represents a technically significant difference to the device described in FIGS. 15 to 16 of U.S. Pat. No. 5,951,493. In the device of the prior art an arrangement of separate lever arms is used to laterally press together the body surface. This has a number of disadvantages. As a result of the distance between the lever arms, the lateral squeezing of the skin surface is incomplete since areas remain untouched between the lever arms. Furthermore in the worst case the skin can get stuck between the lever arm while they move together. Finally it should be noted that the device of the prior art is neither designed nor suitable for fitting snugly to body surfaces of various sizes and shapes. The device is primarily intended to withdraw body fluid from a region of the arm which is less curved compared to the finger pad. The said problems can be avoided by using a pressure-application region made of a deformable material which preferably has a ring shape.

The system for removing body fluid additionally has a perforation device to produce a body opening. Such a perforation device can be a lancet or needle.

In the case of a lancet it is preferably completely removed from the tissue after the incision such that body fluid emerging from the site of incision is accessible. In the case of a needle it can remain at the maximum puncture depth in order to extract body fluid from this depth or it can be withdrawn until it reaches the skin surface in order to take up liquid from this position.

The perforation device can be preferably guided onto the body surface through an opening in the compression unit or the pressure-application region. In order to achieve various depths of incision to allow for various skin types and also to account for the required quantities of blood, it is advantageous to have a variable puncture depth. In order to achieve a defined (and optionally preset) puncture depth it has proven to be particularly advantageous to arrange the perforation device such that it can be displaced relative to the compression unit. This displaceability comprises two aspects which can also be combined. In the first aspect the perforation device is spring loaded relative to the compression unit such that a front face or a stop on the perforation device elastically rests against the body surface when the body part is pressed against the compression unit. The compressive force of the perforation device on the body surface is preferably in the range of 1 to 5 N and is preferably ca. 2 N. If greater compressive forces are used there is a danger that body fluid in the region of the increased internal pressure will be pressed out of this region.

The second aspect i.e. the relative displacement of the perforation device and compression unit concerns a movement of the perforation device into a perforation position and movement away from this position in order to create space to take up body fluid by means of a receiving device. This aspect is particularly important for an integrated system which can be used for blood withdrawal as well as analysis.

In advantageous embodiments of the invention the system for withdrawing body fluid is integrated into an analytical system. Such analytical systems are well-known in the prior art. For example analytical systems named ACCUCHECK PLUS® AND ACCUCHECK ADVANTAGE® are commercially available. As a rule analytical systems which are designed for consumers use disposable test elements which, after contact with a sample liquid, yield a signal which depends on the analyte concentration. In the field of blood sugar measurement optical test elements are used in which the reaction of glucose with a test chemistry leads to a change in colour as well as electrochemical test elements in which an enzymatic conversion of glucose enables an amperometric or potentiometric analysis. The test elements can be advantageously designed such that they actively take up body fluid (e.g. by means of a capillary gap).

The system according to the invention simplifies the integration of a withdrawal unit with an analytical system or for the first time makes an integration possible. As already stated it is customary in the prior art to manually press out the body fluid after producing a skin opening which means that the patient has to remove the body part from the withdrawal device. In contrast a system according to the present invention enables the patient to press the body part against the deformable compression unit and to leave it there in this compressed state to produce a skin opening as well as for the withdrawal. Hence a stronger degree of automation is possible in which the patient only has to press against the compression unit and all subsequent steps up to the read-out of the analytical result can proceed automatically.

Hence an integration of the perforation device and analytical system not only advantageously relates to a spatial integration but also to a process integration which avoids operating steps by the user. Correspondingly such a system also advantageously has a control unit which controls coodinatively activation of the withdrawal device, the withdrawal of body fluid and the transport of body fluid to the analytical system and the analysis.

BRIEF DESCRIPTION OF THE DRAWINGS

Embodiments of systems according to the present invention are elucidated in more detail on the basis of the figures.

DETAILED DESCRIPTION OF THE INVENTION

Figure 1A:
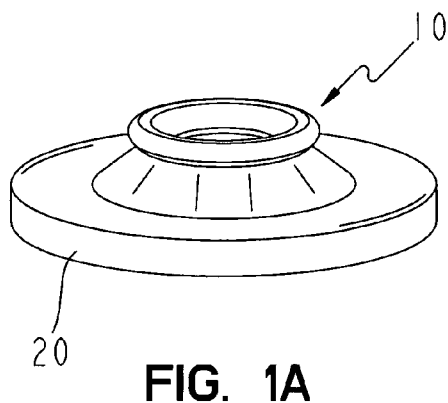
FIG. 1: Compression unit in a perspective and cross-sectional view.
Figure 1B:
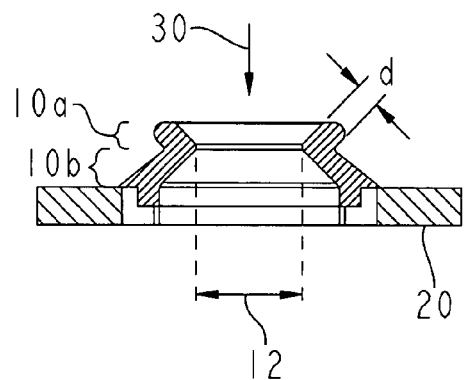

FIG. 1 shows a first embodiment of a deformable compression unit. FIG. 1A shows a perspective diagram of the compression unit (10) which is mounted on a plate (20). The cross-sectional diagram of FIG. 1B shows that the compression unit has two conically tapering regions (10a, 10b) which act as a pressure-application region. The upper pressure-application region (10a) narrows towards the plate (20) and the directly adjoining lower region (10b) widens towards the plate. The compression unit is constructed of a deformable plastic which is polyurethane in the example shown. Silicon and rubber can also be used. It is important that the compression unit can be deformed with sufficient ease as well as being adequately rigid in order to generate the necessary counter-pressure and an adequate pressure in the transverse direction. Suitable materials are in particular those with a hardness of less than 90 Shore preferably less than 50 Shore and particularly preferably in the range of 20 to 40 Shore.

As a result of the structure which in cross-section has the shape of two arrows pointing towards one another and of the deformability, a primary movement (30) of a body part perpendicular to the plate (20) is at least partially converted into a transverse movement. The resulting secondary movement results in a squeezing together of the body part which imitates the milking movement which would otherwise be carried out manually by the user.

Using the compression unit shown in FIG. 1 which has a Shore hardness of 30 it was already possible to obtain a blood volume of 1.5-3 µl from the finger pad with a puncture depth of 0.7 mm in several patients. The amount of blood obtained is essentially determined by the tissue volume pressed together by the compression unit. Due to this limitation the amount of blood is limited and thus hygiene problems caused by too much blood emerging can be avoided.

The present invention is also intended to include arrangements in which a primary movement of the body part relative to the compression unit is at least partially converted into a movement which is perpendicular thereto. Thus for example a system should also be encompassed in which the upper region (10a) of the compression unit is absent and the conversion of the primary into the secondary movement only occurs by means of the lower part (10b). In this connection the term deformable is intended to not only include embodiments whose material is deformable per se as is the case in the embodiment shown in FIG. 1, but also those embodiments are intended to be included whose geometric arrangement is deformed or reshaped by the primary movement. An example of such an embodiment is described in the following in conjunction with FIG. 3.

Figure 2A:
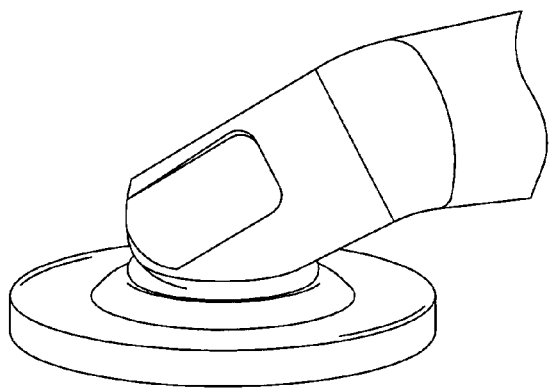
FIG. 2: Compression of a region of the finger tip in a perspective and cross-sectional view.

FIG. 2 shows the operation and action of the compression unit of FIG. 1. As shown in FIG. 2A a body part, preferably a finger tip, is pressed by the user onto the compression unit such that the compression unit is pressed together and the inner width (12) of the compression unit is reduced. As a result a part of the finger tip is squeezed and the internal pressure in this region (50) is increased. The inner width (12) should ideally be in the range of 8 to 11 mm in order to be suitable for large adult fingers as well as children's fingers.

Figure 2B:
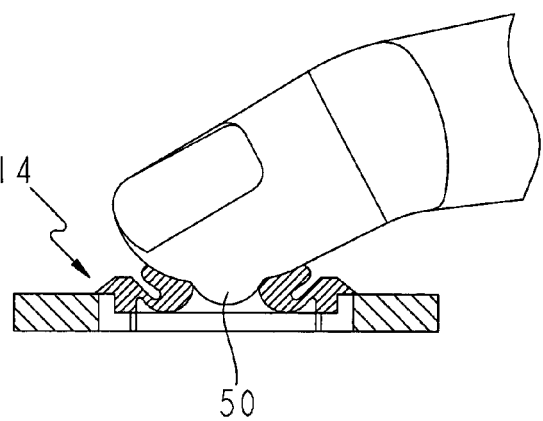

FIG. 2b additionally shows that in this embodiment the pressure-application region (10a, 10b) not only makes a secondary movement parallel to the plate (20) but also becomes arched downwards. This deformation movement of the compression unit amplifies the compression effect within the clamped body region and thus contributes to the desired increase of the internal pressure. A particular advantage of the compression unit containing a pressure-application region made of deformable material shown in FIG. 1 is that it adapts to the contour of the body part. Thus for example it is possible to also withdraw blood from one side of the finger tip which would be virtually impossible with rigid pressure-application devices.

Suitable selection of the wall thicknesses and the hardness of the material enables the partial collapse of the compression unit which occurs when pressure is applied to the compression unit, to be clearly felt by the user. In this manner the user can feel when the pressure is adequate for obtaining blood. However, the basic principle of operation of the compression unit according to the invention remains even when there is not such a discernible collapse of the arrangement.

FIG. 2 shows that in region 14 in which the compression unit (10) is connected to the plate (20), high tensile stresses occur in the compressed state. It has turned out that these tensile stresses are very favourable for the function of the arrangements. Thus it is advantageous to ensure that there is a good frictional linkage between the compression unit and the plate and in particular to durably connect the two components in the region (14).

A further detail which is shown in FIG. 2 is the significance of the thickness (d) of the pressure-application region. In the compressed state the upper and lower pressure-application regions rest against one another and thus lead to an even stronger compression of the body part in the compression unit.

Figure 3:
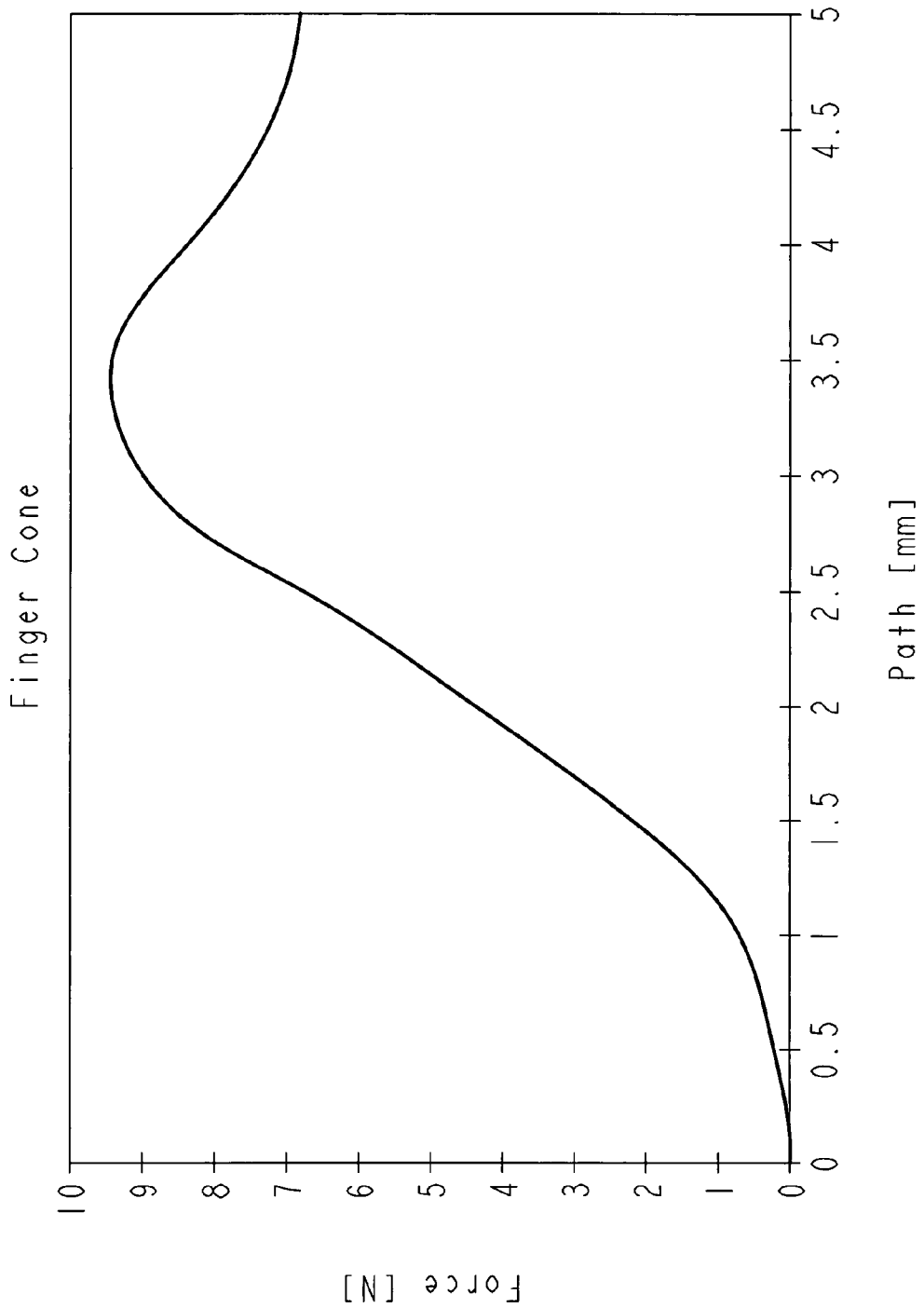
FIG. 3: Path-force diagram when a finger is pressed against a compression unit according to FIG. 1.

The above-mentioned collapsible effect of the compression unit is shown in FIG. 3. The abscissa shows the path of a finger tip relative to the compression unit in mm. The repulsive force between the finger and compression unit is shown on the ordinate. FIG. 3 shows that when the finger starts to press the repulsive force increases, passes through a maximum and decreases again as it approaches further. In this case the position 5 mm corresponds to the state shown in FIG. 2. Overcoming the force maximum is felt by the user as a collapse which at the same time indicates to him that he has guided his finger sufficiently firmly and far enough onto the compression unit. The transition through a force maximum is also advantageous since this causes the user to leave his finger pressed onto the compression unit for the duration of the perforation and optionally the blood withdrawal.

Figure 4A:
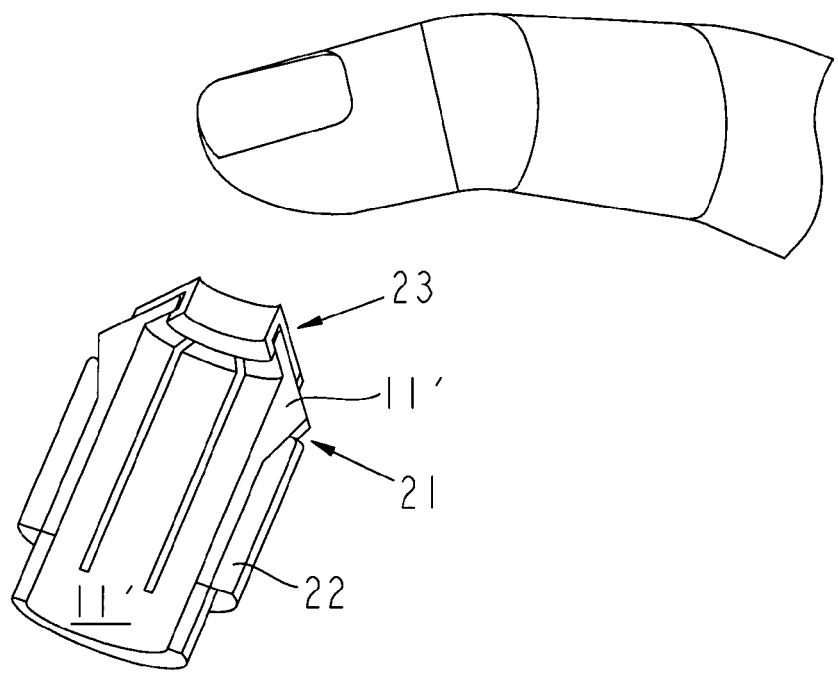
FIG. 4: Cross-sectional diagram of a further embodiment of a compression unit.
Figure 4B:
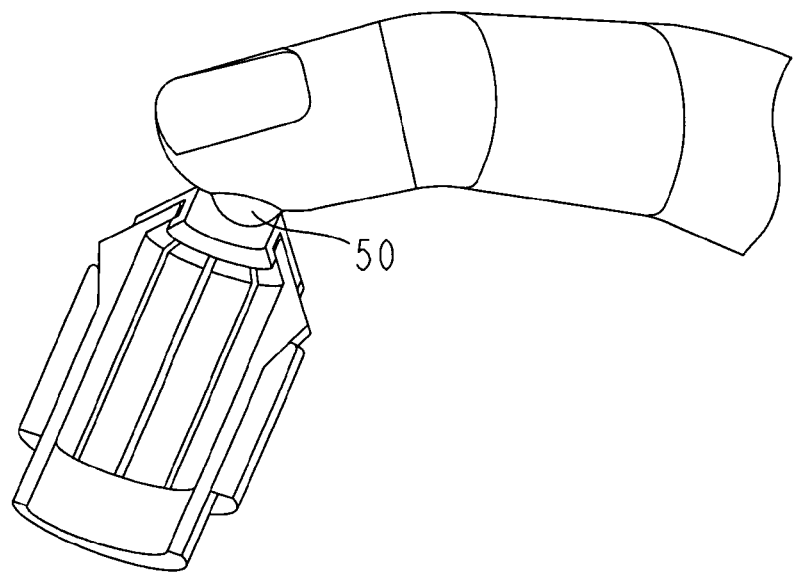

FIG. 4 shows a similar embodiment to that in FIGS. 1 and 2 in which, however, the compression unit is constructed of rigid elements which are bent by the pressure of the body part such that the geometric structure of the compression unit as a whole is deformed. The compression unit of FIG. 4 has a plurality of lamellae (11') which are spaced from one another. The lamellae have a bevel (21) on their outer side by means of which they move together when the unit of lamellae is inserted into the clamping ring (22) by applying pressure. In the pressure-application region the lamellae (11') are covered by a cap (23) made of an elastic material. Hence also in this embodiment the primary pressing movement of the finger generates a secondary movement laterally to the primary pressing direction which results in a lateral pressing together of the skin surface. The production of an increased internal pressure (50) of a body region is also shown in FIG. 4B. The cap (23) made of an elastic material has the effect on the one hand, that the skin cannot be pinched between the lamellae and also adapts the compression unit to the geometry of the pressed body part.

Figure 5:
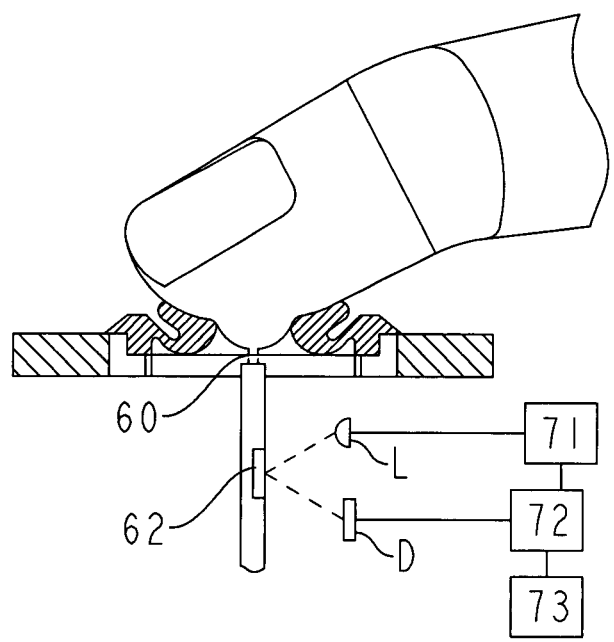
FIG. 5: Integrated system for the analysis of body fluids with a compression unit according to FIG. 1.

FIG. 5 shows an integrated system for the analysis of body fluid which comprises a compression unit according to FIG. 1. As already stated above the compression unit has an opening between which the compressed region of the body part is located. The perforation device can access the body part in order to make a skin incision and body fluid can be withdrawn through this opening in the compression unit. In the embodiment shown in FIG. 5 the perforation device comprises a cannula (60) which is inserted into the compressed region and remains there to collect body fluid. The cannula (60) is connected to an analytical zone (62) which changes colour in the example shown depending on the analyte concentration. For the analysis this analytical zone (62) is irradiated with a light source (L) and reflected radiation is detected by a detector (D). The light source is controlled by a control unit (71) and the signal of the detector is evaluated by an evaluation unit (72). The evaluation unit (72) preferably also controls the control unit (71). The evaluation unit (72) evaluates the detector signal in order to determine the concentration of the analyte contained in the body fluid. The analytical result is displayed by an output unit (73) for example an LC display.

Figure 6:
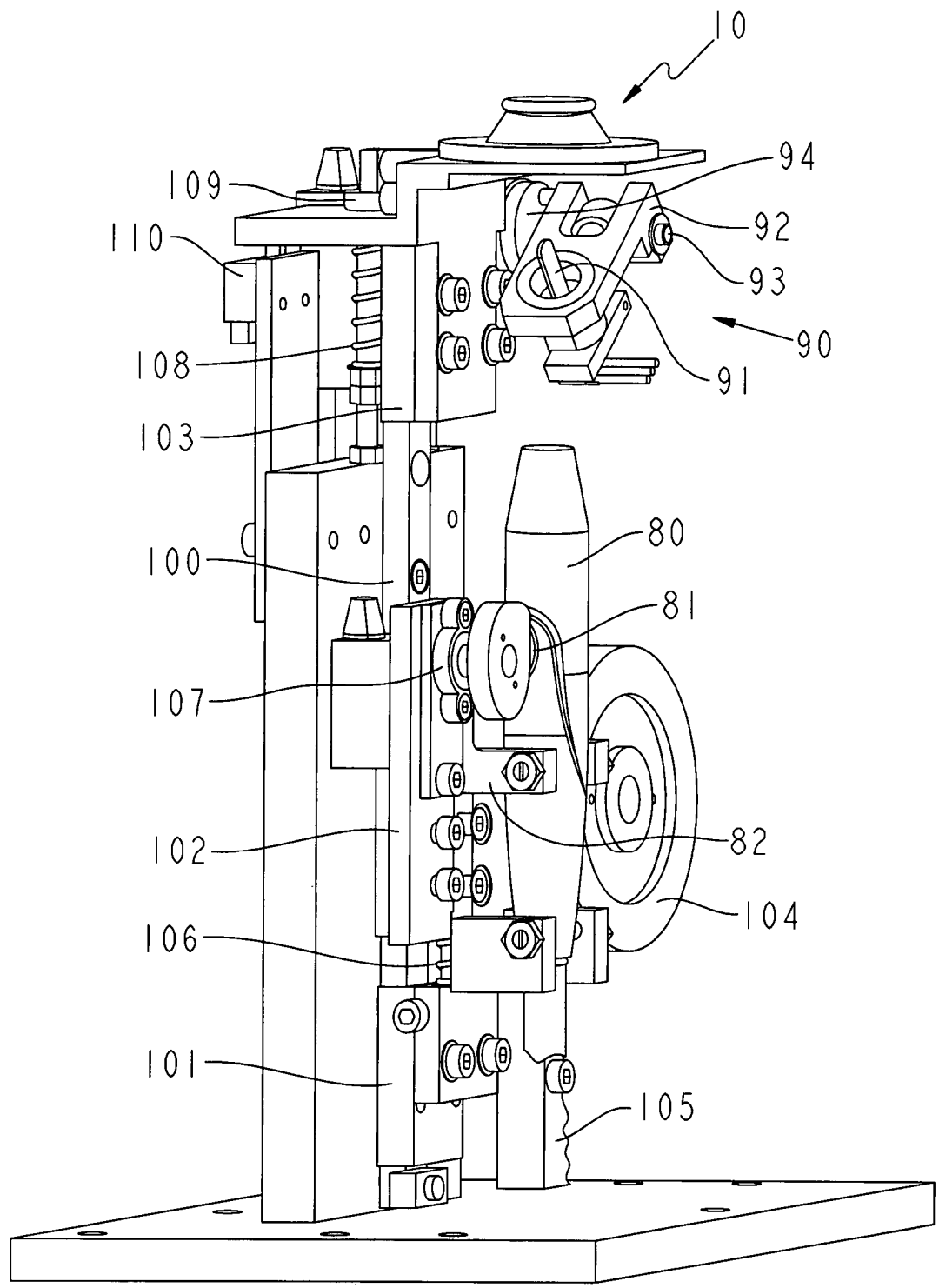
FIG. 6: Integrated system for the analysis of body fluids comprising a compression unit, a perforation unit and an analytical unit.

FIG. 6 shows an integrated system in which the skin perforation and subsequent blood withdrawal for analysis occurs completely automatically. The system comprises three functional units i.e. a compression unit (10), a perforation device (80) and an analytical system (90). The said units are displaceably mounted on a linear guide unit (100). The linear guide unit is composed of a guide rail (100) with three slides attached movably thereto (101, 102, 103). The first slide (101) is moved by a server drive (not shown in the selected view) via a gearwheel (104) and a gear rod (105). A spring (106) transmits the movement of the first slide (101) to the second slide (102) with a lancing device (80) attached thereto. The pressure of the lancing device on the finger can be achieved independently of the distance with approximately constant force as a result of the spring. The force should not exceed ca 2N. If the forces are larger there is a risk that during the pressing and lancing blood that has already accumulated in the finger tip will be squeezed out of the compressed volume. This would hence reduce the amount of blood that can be potentially obtained. A trigger button (81) on the lancing device can be operated by a servodrive (107) with a cam disk. The compression unit (10) is mounted on the third slide (103) and is pressed against an upper stop (109) by means of an adjustable spring (108) of ca. 10-15 N. The force exerted by the finger of the user moves the third slide (103) downwards against a limit switch (110). If the end position where the third slide presses against the limit switch is not reached, the subsequent operation process is not enabled. For this purpose the limit switch is connected to a process control unit which controls activation/actuation of the system units. The system also includes an analytical unit (90) containing a test strip (91) which is pivotally mounted in a holder (92) on a drive shaft (93). The transfer of torque from the drive shaft to the holder (92) is accomplished by a lever spring. The force with which the test strip presses on the finger is thus almost independent of the angle of rotation. The pressing force is ca. 1N and should not substantially exceed this value. Excessive pressing forces seal the puncture channel that has been produced and in addition displace the dammed up blood volume in the sealed compressed tissue. The servodrive (94) which drives the drive shaft (93) can only be partially seen in the selected view.

Procedure for carrying out a measurement: A lancet is inserted in the perforation device (lancing device 80), the lancing device is tensioned (can occur automatically). Then the lancing device is placed in the holder (82). An unused test strip (91) is placed in the holder (90).

In the initial state the holder (92) is in a position which enables movement of the lancing device towards the compression unit (10) (swung back). For carrying out a perforation the lancing device is inserted so far into the compression unit that the end of the lancing device can be felt by the user when the compression unit is applied and pressed down. The pressing force of the lancing device is controlled (ca. 2N) in this position by the spring (106). The external force applied by the user on the finger cone is registered by means of a spring (108) and limit switch (110) and is monitored during the whole measurement (10-15 N). Removal of the finger leads to termination of the measurement.

If the user has positioned his finger optimally, the measurement process can start or the measurement process is started automatically.

The servodrive (107) actuates the trigger button of the lancing device (80). Immediately after the lancing process the lancing device is moved away from the finger tip and positioned such that the analytical device can be moved without hindrance. During a waiting period of 3-10 sec a portion of the dammed blood volume emerges from the incision wound and forms a drop on the skin surface. After the waiting period the analytical unit is swung onto the skin surface in such a manner that opening of the test strip dips into the blood drop. In this process the maximum pressing force of ca. 1N is regulated by the lever spring. As soon as the test field of the test strip is adequately wetted, the user is informed by the analytical electronics that he can remove his finger. The measurement result obtained is displayed on an LCD.

What is claimed is:

1. A lancing device comprising a compression unit for stimulating the efflux of a body fluid from a body part, the compression unit having a pressure-application region made of a deformable material, the pressure-application region comprising an opening with a rim, wherein the width of the opening is reduced as the body part is pressed against the rim, wherein the compression unit includes a plate and the pressure-application region includes a lower conically tapering region widening towards the plate and an upper conically tapering region narrowing towards the plate.

2. The device of claim 1 wherein the pressure-application region is formed to increase the repulsive force as the body part is pressed against the compression unit.

3. The device of claim 1, wherein the upper and lower conically tapering regions are formed to cooperate so that the primary movement of the body part against the upper conically tapering region perpendicular to the plate is at least partially converted into a transverse movement.

4. The device of claim 1 wherein the deformable material of the pressure-application region is an elastomer.

5. The device of claim 1 wherein the rim is in the form of a ring.

6. The device of claim 1, wherein the opening has an inner width in the range of at least 8 mm-11 mm.

* * * * *